United States Patent [19]

Karniel

[11] Patent Number: Plant 6,464

[45] Date of Patent: Dec. 13, 1988

[54] **GRAPEVINE VARIETY, *VITIS VINIFERA*, PRODUCING SEEDLESS GRAPES WITH A LONG SHELF-LIFE, NAMED KING HUSAINY**

[75] Inventor: Mordechai Karniel, Zichron Yaacov, Israel

[73] Assignee: Zanzivivai-Ferrara S.r.l., Fossanova San Marco, Italy

[21] Appl. No.: 910,144

[22] Filed: Sep. 22, 1986

[51] Int. Cl.[4] ..... A01H 5/03

[52] U.S. Cl. ..... Plt./47

[58] Field of Search ..... Plt./47

[56] References Cited

U.S. PATENT DOCUMENTS

P.P. 5,856 1/1987 Garabedian ..... Plt. 47

*Primary Examiner*—Robert E. Bagwill

*Attorney, Agent, or Firm*—Martin A. Levitin

[57] ABSTRACT

A new and distinct asexually reproduced grapevine variety, as illustrated and described. The plants are very vigorous, very productive with very large, green-yellow colored, seedless berries and with few falling berries. No thinning is needed. The fruit of this variety has a medium ripening time, a long shelf-life and can be harvested in early July under the conditions existing in Israel.

1 Drawing Sheet

DESCRIPTION OF THE INVENTION

The present invention relates to a novel asexually reproduced grapevine variety, *Vitis vinifera*, of seedless table grapes with a long shelf-life, named King Husainy.

Among the table grapevine varieties this variety is appreciated for its large berry size, for being seedless and very productive. It shows no berry shedding and it is resistant to rotting.

This variety was obtained by its breeder in the Karniel vineyard, Zichron Ya'acov, Israel, through selection started in 1980, cultivation for one generation and analysis for a period of five years. For propagation, grafting on Rogery 140 rootstock was used. A variety was obtained producing table grapes having a berry size of 40×18 mm with green-yellow colored seedless berries, very productive, with no berry shedding and resistant to rotting.

The drawing shows a color photograph of the new variety, as well as a leaf of the same.

DESCRIPTION

Vine

General: Large size, vigorous, horizontal canes, hardy and productive.

Trunk: Big and thick.

Bark: Light brown color, long strip.

Canes:

*Length* 2.5 *M with basis.*—16 mm

*Width at node.*—15 mm.

*Width at internode.*—14 mm.

Nodes:

*Average distance between the nodes.*—5–7 cm.

Tendrils:

*Short.*—Average length — 10–15 cm.

*Thickness.*—Thin — medium, average thickness — 2 mm.

*Location.*—Discontinuous.

*Leafing.*—Some produce leaves.

Color: (Matured Cane) Deep brown.

Foliage

Density: Heavy.

Leaves: From 9th to 12th node.

Flowers

Size: Large.

*Location (node where fruit is produced.*—Mostly 1st–3rd node).

Type: Fertile.

Bloom:

*Date of first bloom.*—May 7.

*Full bloom.*—May 19.

*Last bloom.*—May 28.

Pedicel: Green color.

*Smoothness.*—Smooth.

Fruit

Peduncle: Short, most of clusters spread to two after one (1) cm for two arms of one cluster.

Cluster: Conical medium, mostly split to two similar sides. Very loose.

*Number of clusters per cane.*—2–3.

*Average weight.*—580 grams.

*Berry.*—Very large size, dimensions — 40×18 mm.

*Berry set.*—Medium.

*Fruiting habit.*—Very productive.

*Thickness of skin.*—Thin.

*Texture of skin.*—Very light.

*Color.*—Green yellow.

*Berry texture.*—Very firm, crispy.

*Flavor.*—Neutral.

*Traces of seeds.*—None.

*Period of ripening.*—July 10, about one week after Superior seedless and two weeks before Thompson seedless.

What is claimed is:

1. A new and distinct asexually reproduced grapevine variety, extremely vigorous and highly productive, characterized by very large, green-yellow colored, seedless berries with a long shelf-life, few falling berries and not requiring thinning, substantially as illustrated and described.

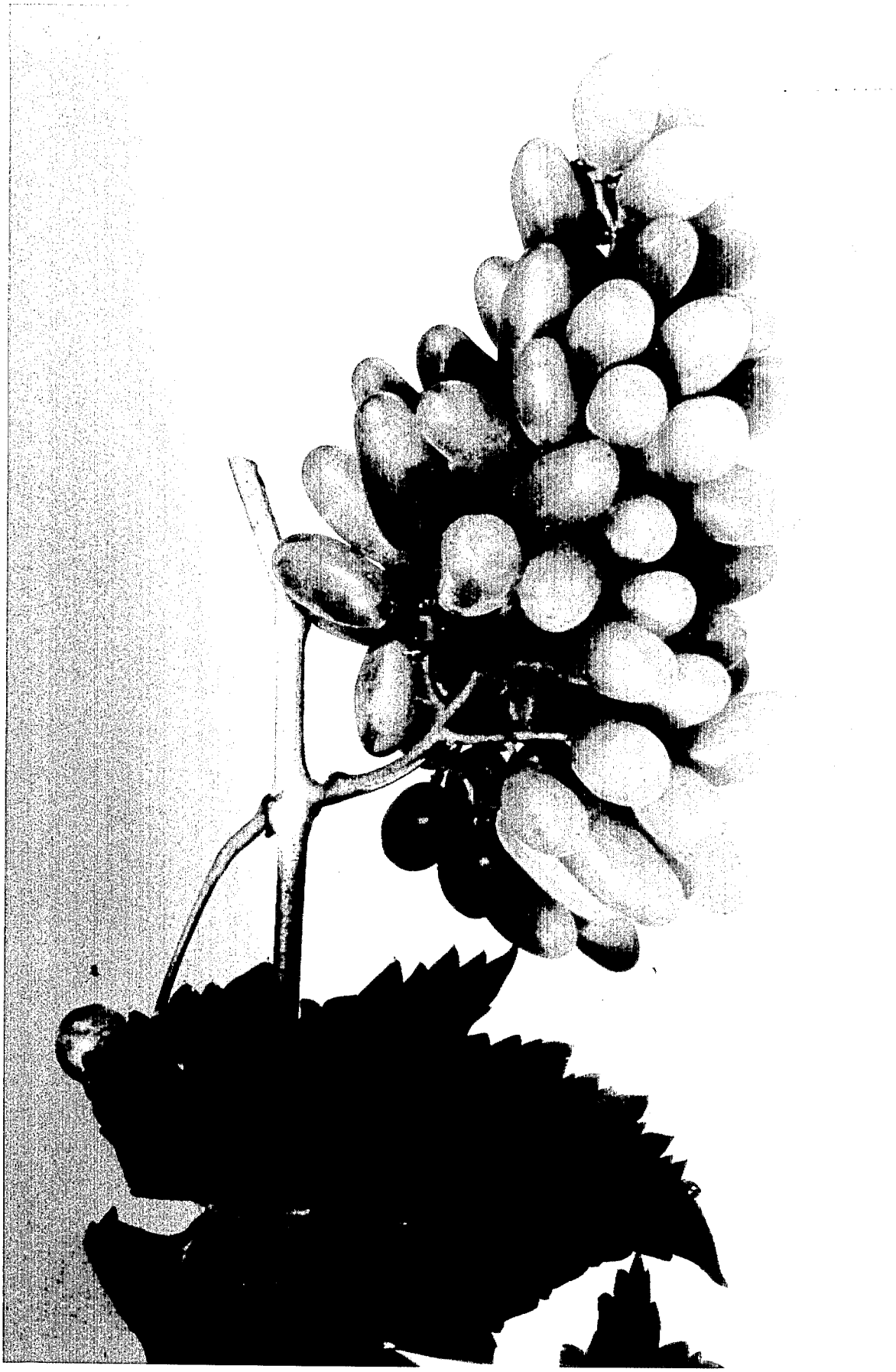

* * * * *